US010430905B2

(12) United States Patent
Hisanaga et al.

(10) Patent No.: US 10,430,905 B2
(45) Date of Patent: Oct. 1, 2019

(54) CASE SEARCH DEVICE AND METHOD

(71) Applicants: FUJIFILM Corporation, Tokyo (JP); SHIZUOKA PREFECTURE, Shizuoka, Shizuoka (JP)

(72) Inventors: Ryuji Hisanaga, Tokyo (JP); Masahiro Endo, Shizuoka (JP)

(73) Assignees: FUJIFILM CORPORATION, Tokyo (JP); SHIZUOKA PREFECTURE, Shizuoka, Shizuoka (JP)

( * ) Notice: Subject to any disclaimer, the term of this patent is extended or adjusted under 35 U.S.C. 154(b) by 509 days.

(21) Appl. No.: 13/848,656

(22) Filed: Mar. 21, 2013

(65) Prior Publication Data

US 2013/0253953 A1 Sep. 26, 2013

(30) Foreign Application Priority Data

Mar. 23, 2012 (JP) ................. 2012-067600

(51) Int. Cl.
*G06Q 50/24* (2012.01)
*G16H 50/70* (2018.01)
*G06F 19/00* (2018.01)

(52) U.S. Cl.
CPC ........... *G06Q 50/24* (2013.01); *G06F 19/321* (2013.01); *G16H 50/70* (2018.01)

(58) Field of Classification Search
CPC ........ G06Q 10/00; G06Q 50/00; G16H 10/00; G16H 15/00; G16H 20/00; G16H 30/00; G16H 40/00; G16H 50/00; G16H 70/00; G16H 80/00; G16H 10/40; G16H 20/10; G16H 20/13; G16H 20/17

USPC ................................. 705/2, 3, 20
See application file for complete search history.

(56) References Cited

U.S. PATENT DOCUMENTS 7,827,158 B2 * 11/2010 Hayakawa ................... 707/696
2001/0043729 A1 * 11/2001 Giger et al. .................. 382/128
2002/0159637 A1 * 10/2002 Echigo .............. G06F 17/30905
382/190

(Continued)

FOREIGN PATENT DOCUMENTS

JP  2001-117936 A   4/2001
JP  2003-325458 A   11/2003

(Continued)

OTHER PUBLICATIONS

Notice of Reasons for Rejection dated Mar. 12, 2014 (with Partial English language Translation).

(Continued)

*Primary Examiner* — Robert W Morgan
*Assistant Examiner* — Charles P Coleman
(74) *Attorney, Agent, or Firm* — McGinn I.P. law Group, PLLC.

(57) ABSTRACT

Image search conditions that are past search conditions are displayed in an image search history area, and text search conditions are displayed in a text search history area. When a user selects a desired image search condition out of the search conditions displayed in the image search history area, and selects a desired text search condition out of the search conditions displayed in the text search history area, case data that matches the selected image search condition and the text search condition is extracted from a database and displayed in a search result display area.

15 Claims, 8 Drawing Sheets

(56) References Cited

U.S. PATENT DOCUMENTS

| | | | |
|---|---|---|---|
| 2003/0013951 A1* | 1/2003 | Stefanescu | G06F 17/30256 600/407 |
| 2003/0194131 A1* | 10/2003 | Zhao | G06K 9/46 382/190 |
| 2004/0003001 A1 | 1/2004 | Shimura | |
| 2005/0149360 A1* | 7/2005 | Galperin | G06F 17/30247 705/2 |
| 2006/0143154 A1* | 6/2006 | Jager | G06F 17/30011 |
| 2007/0031015 A1* | 2/2007 | Chen | G06T 7/0012 382/128 |
| 2007/0077025 A1* | 4/2007 | Mino | G06F 17/30256 386/241 |
| 2008/0034020 A1* | 2/2008 | Hayakawa | G06F 17/30646 |
| 2009/0080734 A1* | 3/2009 | Moriya et al. | 382/128 |
| 2009/0082637 A1* | 3/2009 | Galperin | G06F 19/321 600/300 |
| 2009/0097756 A1* | 4/2009 | Kato | G06F 17/30256 382/190 |
| 2009/0180693 A1* | 7/2009 | Desai | G06T 7/12 382/173 |
| 2009/0274384 A1* | 11/2009 | Jakobovits | G06F 17/3028 382/254 |
| 2010/0228727 A1* | 9/2010 | Hisanaga | G06F 19/321 707/723 |
| 2010/0274776 A1* | 10/2010 | Iizuka | G06F 17/30247 707/706 |
| 2013/0311502 A1* | 11/2013 | Takata | G06F 17/30253 707/758 |
| 2014/0355882 A1* | 12/2014 | Hayata | G06T 7/0081 382/173 |
| 2015/0347505 A1* | 12/2015 | Ohashi | G06F 19/321 707/754 |
| 2015/0356271 A1* | 12/2015 | Kozuka | G06F 19/3443 705/2 |
| 2016/0098613 A1* | 4/2016 | Mino | G06F 17/30256 382/190 |
| 2018/0004806 A1* | 1/2018 | Ohashi | G06K 9/6215 |

FOREIGN PATENT DOCUMENTS

| | | |
|---|---|---|
| JP | 2004-5364 A | 1/2004 |
| JP | 2004-157623 A | 6/2004 |
| JP | 2009-93563 A | 4/2009 |
| JP | 2010-250529 A | 11/2010 |
| JP | 2011-115279 A | 6/2011 |
| JP | 2011-138263 A | 7/2011 |

OTHER PUBLICATIONS

Daijiro Komaki et. al, "Exploring Information Sharing Functions for Mobile Collaborative Web Search," The Technical Report of the Institute of Electronics, Information and Communication Engineers, Japan, The Institute of Electronics, Information and Communication Engineers (IEICE), Dec. 9, 2011, vol. 111, Issue No. 361, pp. 7-12.

* cited by examiner

CASE SEARCH DEVICE AND METHOD

BACKGROUND OF THE INVENTION

Field of the Invention

The present invention relates to a case search device and method, and more particularly relates to a technology of searching for case data with use of image search and text search.

Description of the Related Art

Conventionally, health care professionals such as doctors perform a physical examination of patients based on diagnosing images obtained from medical diagnostic imaging devices such as CT and MRI devices. In such diagnostic imaging, diagnostic accuracy can be enhanced by referring to diagnostic data on diagnosing images taken in past examinations. Accordingly, diagnosing images taken in the past and diagnostic data thereon are accumulated in a database as case data, and case data similar to a diagnosing image are retrieved from the database.

For example, Japanese Patent Application Laid-Open No. 2004-5364 discloses a technology to provide an ROI (region of interest) within an object image, to search for similar image data, which has an image characteristic similar to that of image data P' on the ROI, and diagnostic data thereon, and to display search results on a monitor.

In Japanese Patent Application Laid-Open No. 2001-117936, a technology is described which is to set a region of interest in an inputted three-dimensional image, to calculate a feature value of the region of interest, and to extract similar images with use of the feature value.

Further, Japanese Patent Application Laid-Open No. 2003-325458 discloses a technology to search for image data P2, which represents a similar case of the case in image data P1 that is a diagnosis target, by image analysis, to search for diagnostic data D2 relevant to the image data P2 and diagnostic data D3 including disease state information similar to the disease state information on the image data P1, to determine candidate disease information on the image data P1 with use of the diagnostic data D2 and D3, and to output it to a display device.

According to these technologies, it becomes possible to appropriately search for the cases similar to a diagnosing image from a database having a large number of images.

However, in the technologies of Japanese Patent Application Laid-Open No. 2004-5364 and Japanese Patent Application Laid-Open No. 2001-117936, when multiple image searches are performed for one diagnosing image with its ROI varied, search results prior to ROI variation are not immediately reflected, so that a search needs to be repeated under the same condition.

Also in the case of performing multiple image searches and then performing multiple text searches in the technology of Japanese Patent Application Laid-Open No. 2003-325458, the text searches are to be performed against the results of a past image search, which is a cumbersome operation disadvantageously taking time and effort.

The present invention has been made in view of such circumstances, and an object of the present invention is to provide a device and method for case search which can enhance search efficiency by allowing easy reference to past search histories.

SUMMARY OF THE INVENTION

In order to accomplish the above object, one aspect of a case search device includes: a database which stores case data including image data and text data; an image acquiring device adapted to acquire a diagnosis target image; an area extracting device adapted to extract an area of interest from the acquired diagnosis target image; a text data acquiring device adapted to acquire text data relating to the diagnosis target image; a search device adapted to perform against the database an image search with the extracted area of interest as an image search condition and a text search with the acquired text data as a text search condition and to extract case data that matches the image search condition and the text search condition; a search result display device adapted to display the extracted case data on a display device; a search condition storing device adapted to store each of the image search condition and the text search condition; and a search history display device adapted to display on the display device each of the stored image search conditions and text search conditions so as to be specifiable by a user, wherein when any one of the displayed image search conditions and any one of the displayed text search conditions are specified, the search device extracts case data that matches the specified image search condition and the specified text search condition.

According to this aspect, each of the image search conditions and text search conditions which were used in past searches is displayed on the display device so as to be specifiable by a user. Once any one of the displayed image search conditions and any one of the text search conditions are specified, case data that matches the specified image search condition and text search condition is extracted from the database. As a result, the user can easily select a past search condition so that search efficiency can be enhanced.

The area extracting device preferably extracts an area of interest based on an instruction by the user. Accordingly, it becomes possible to perform a search in an appropriate area of interest.

It is preferable that the area extracting device extracts the area of interest by conducting image analysis based on a specified threshold. As a consequence, an area of interest can automatically be extracted, so that a search can be performed in a more appropriate area of interest.

It is preferable that the text data acquiring device acquires text data inputted by the user with an input device. Accordingly, it becomes possible to perform a search with appropriate text data.

It is preferable that the search device calculates a feature value regarding the extracted area of interest, compares the calculated feature value with a feature value of image data on an identical region in the case data included in the database to calculate a similarity degree, and performs an image search based on the calculated similarity degree. Accordingly, an appropriate image search can be performed.

It is preferable that the search device extracts case data from the case data obtained by the text search in order of higher similarity degrees. Accordingly, it becomes possible to present appropriate search results to the user.

It is preferable that the search condition storing device stores the calculated feature value as the image search condition. Accordingly, it becomes possible to display appropriate image search conditions as a history.

It is preferable that the search condition storing device stores a search result by the search device. Accordingly, when a past search condition is selected, search results can be displayed without the necessity of re-execution of a search.

It is preferable that the search history display device displays on the display device the stored image search conditions and text search conditions in a matrix. Accordingly, it becomes possible to present a search history in a way that the user can easily understand.

It is preferable that the search result display device displays image data and text data in the extracted case data. Accordingly, it becomes possible to present appropriate search results to the user.

In order to accomplish the above-stated object, one aspect of a method for case search includes: an image acquisition step of acquiring a diagnosis target image; an area extraction step of extracting an area of interest from the acquired diagnosis target image; a text data acquisition step of acquiring text data relating to the diagnosis target image; a search step of performing against a database storing case data including image data and text data an image search with the extracted area of interest as an image search condition and a text search with the acquired text data as a text search condition and extracting case data that matches the image search condition and the text search condition; a search result display step of displaying the extracted case data on a display device; a search condition storage step of storing each of the image search condition and the text search condition in a storing device; and a search history display step of displaying on the display device each of the stored image search conditions and text search conditions so as to be specifiable by a user, wherein in the search step, when any one of the displayed image search conditions and any one of the displayed text search conditions are specified, case data that matches the specified image search condition and the specified text search condition is extracted.

In order to accomplish the above-stated object, one aspect of a non-transitory programmable storage medium tangibly embodying a program of machine-readable instructions executable by a digital processing apparatus to perform a case search method, said method comprising: an image acquiring function to acquire a diagnosis target image; an area extracting function to extract an area of interest from the acquired diagnosis target image; a text data acquiring function to acquire text data relating to the diagnosis target image; a search function to perform against a database storing case data including image data and text data an image search with the extracted area of interest as an image search condition and a text search with the acquired text data as a text search condition and to extract case data that matches the image search condition and the text search condition; a search result display function to display the extracted case data on a display device; a search condition storing function to store each of the image search condition and the text search condition in a storing device; and a search history display function to display on the display device each of the stored image search conditions and text search conditions so as to be specifiable by a user, wherein in the search function, when any one of the displayed image search conditions and any one of the displayed text search conditions are specified, case data that matches the specified image search condition and the specified text search condition is extracted.

Thus, a storage medium storing a program for causing a computer to execute the case search functions is also included in the present invention.

According to the present invention, search efficiency can be enhanced by allowing easy reference to past search histories.

DETAILED DESCRIPTION OF THE PREFERRED EMBODIMENTS

Hereinafter, preferable embodiments of the present invention are described in detail with reference to accompanying drawings.

<Configuration of Case Search Device>

Figure 1:
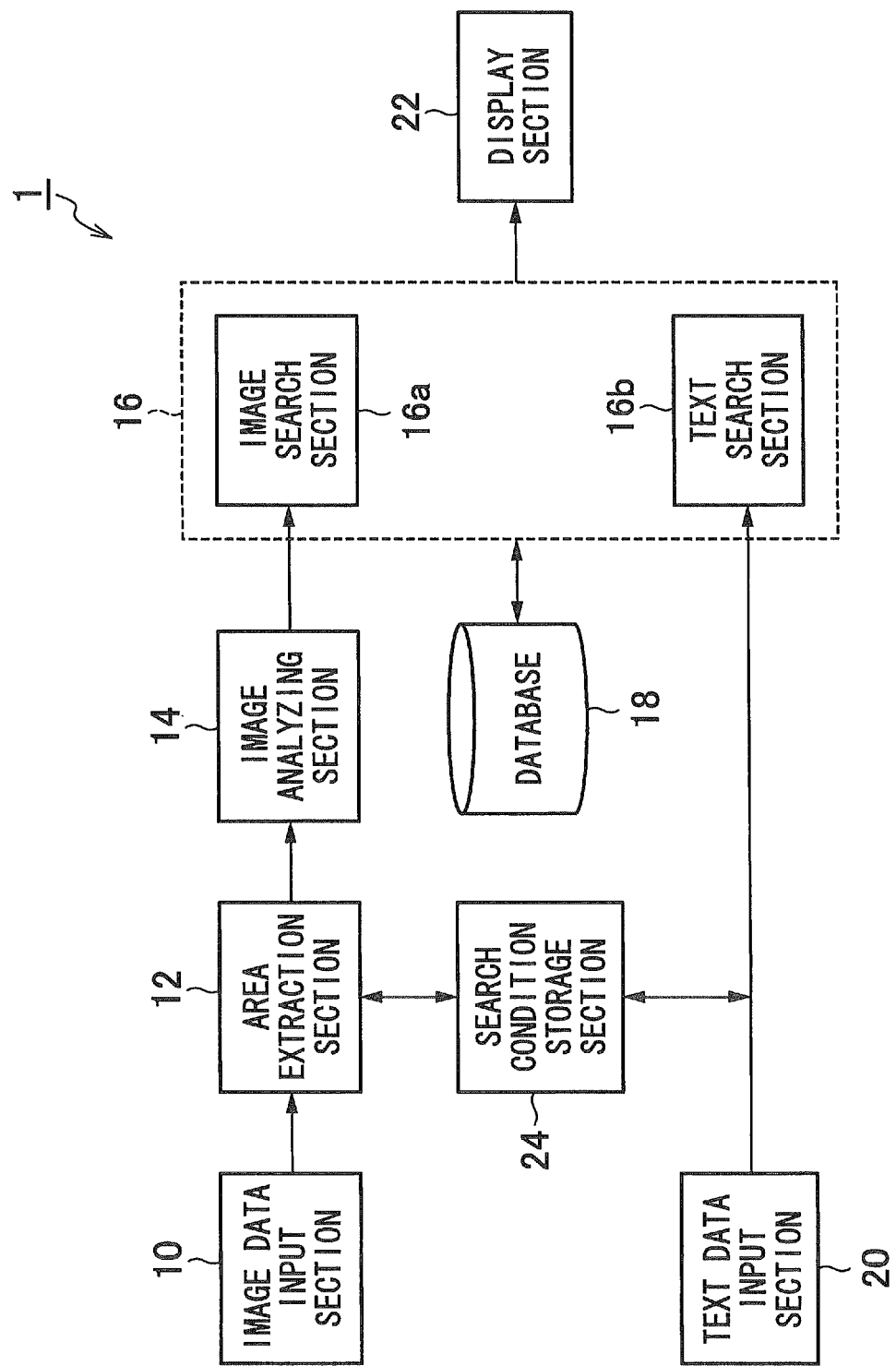
FIG. 1 is a view showing one example of an overall configuration of a case search device.

FIG. 1 is a view showing one example of an overall configuration of a case search device 1 according to the present embodiment. As shown in the drawing, the case search device 1 includes an image data input section 10, an area extraction section 12, an image analyzing section 14, a case search section 16, a database 18, a text data input section 20, a display section 22, and a search condition storage section 24. The case search device 1 is a device adapted to search for case data having a lesion portion similar to the lesion portion of a diagnosing image obtained by a diagnosis and displays the retrieved case data in a referable way.

The image data input section 10 (equivalent to the image acquiring device) receives an input of diagnosing image data obtained from various medical diagnostic imaging devices, such as CT, MU and X-ray images, and US, endoscope, and pathology images. The diagnosing image may be an image including attendant information (such as a size and image pick-up date and time) according to a specified standard such as DICOM (Digital Imaging and Communications in Medicine).

Image data may be inputted through recording media, such as DVDs, USB memory devices, and memory cards, or may be inputted via wireless and wired networks. It is also possible to store image data in the database 18 in advance and to read and input the data from the database 18.

The area extraction section 12 (equivalent to the area extracting device) extracts an area of interest suspected to be a lesion portion from the image data inputted from the image data input section 10. Extraction may be conducted by encircling the area of interest with an input device such as a mouse, or may manually be performed by such operation as inputting a coordinate or range of the area of interest, or an area specified with a semiautomatic mouse or the like may be extracted by image analysis as described in "A Machine learning approach for interactive lesion segmentation", Proceedings of the SPIE, Volume 6512, pp. 651246 (2007) by Y. Li, S. Hara, W. Ito, and K. Shimura. Further, a method involving automatic detection as described in Japanese Patent Application Laid-Open No. 2005-198887 and Japanese Patent Application Laid-Open No. 2005-246032 may also be employed.

Figure 2:
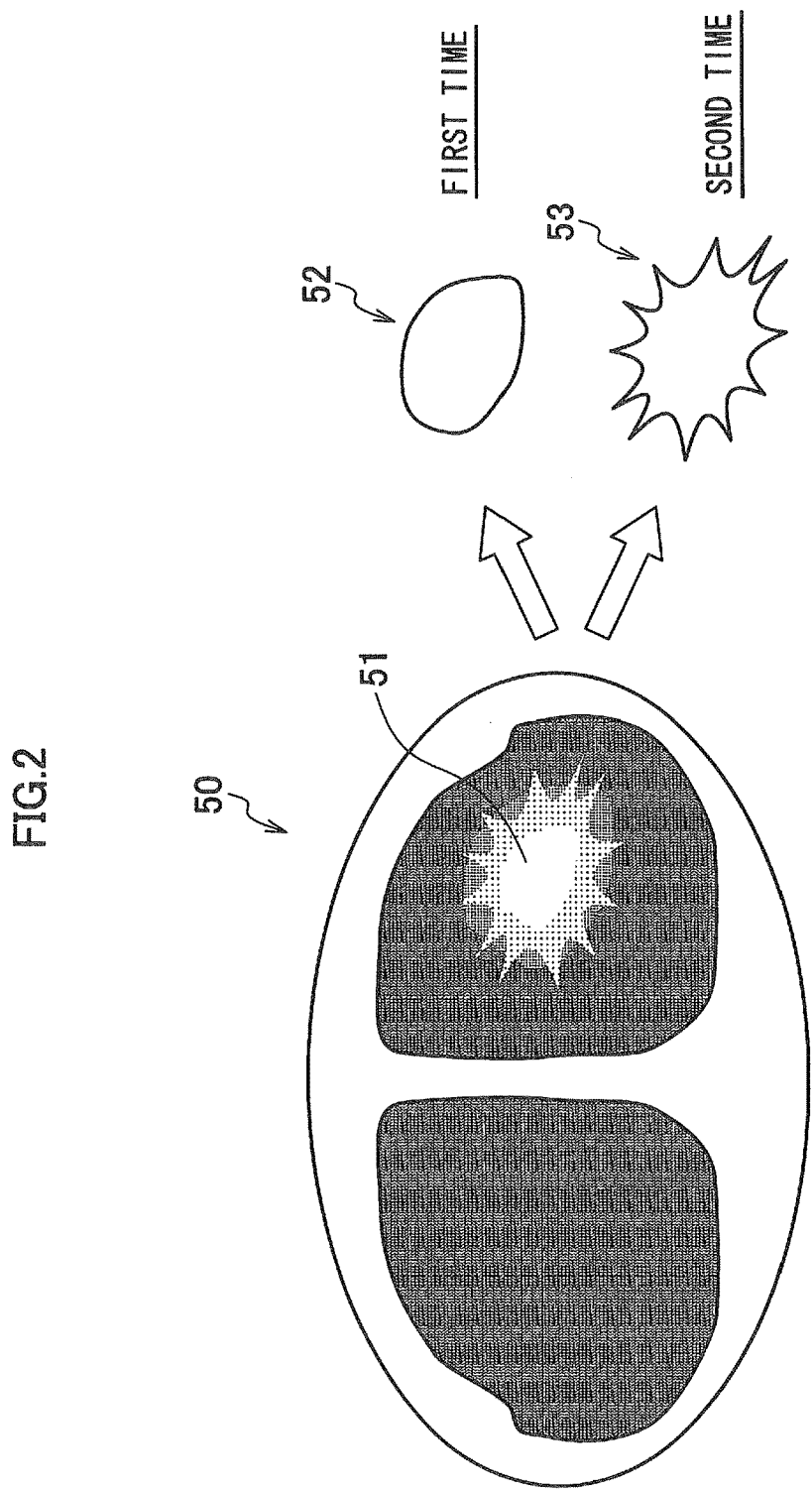
FIG. 2 is a view for explaining area extraction.

FIG. 2 is a view showing area extraction. In this drawing, an area of interest 52 and an area of interest 53 for a portion 51 suspected to be a lesion portion in image data 50 are extracted under different extraction conditions.

It goes without saying that the shape of extraction can be changed when an area of interest is manually extracted. However, even when area extraction is automatically performed, the shape of the area of interest can be varied by changing a threshold for use in signal processing executed for area extraction.

The image analyzing section 14 analyzes image data on the area of interest extracted by the area extraction section 12, and calculates a feature value required for a search. Examples of the calculated feature value include: features regarding pixel values such as an average value, a distribution, a maximum value, a minimum value and a luminance histogram within image data; positions; numeric values with respect to shapes, such as a circularity degree of a profile, a moment, a cross sectional radius, a volume, and an area; and shape information and texture information on a lesion portion in the area of interest, which is obtained by a method described in "Active Appearance Models" in Proc. 5th European Conference on Computer Vision, Germany, Springer, 1998, vol. 2, p.p. 484-498 by T. F. Cootes, G. J. Edwards, C. J. Taylor and which is obtained by various filtering processing.

The feature value may also be a function (or a threshold) which discriminates a certain feature. A method for setting this discriminant function is not particularly limited. For example, a linear or nonlinear discriminant function used for publicly known class sorting, such as statistical methods using known data (learned data) such as SVM (support vector machine), may be used (see, for example, "An Introduction to Support Vector Machines" by Nello Cristianini and John Shawe Taylor, KYORITSU SHUPPAN CO., LTD. as a reference).

The case search section 16 (equivalent to the search device) is adapted to search for similar cases in the database 18 based on an inputted search condition, and includes an image search section 16a and a text search section 16b.

The database 18 is a so-called case database, in which respective cases are registered with data such as image data, area of interest information, image feature information and diagnostic data (text data) being associated thereto.

The image data is diagnosing image data taken in a past diagnosis. The image data is the same as the image data on a diagnosing image inputted from the image data input section 10. The area of interest information is information such as a coordinate that represents an area of interest in corresponding image data.

The image feature information is information acquired from corresponding image data and is used for an image search. The image feature information includes the feature value of an area of interest calculated by the image analyzing section 14 when image data is registered into the database 18.

The image search section 16a searches for a similar image from image data on an identical region registered into the database 18 based on an analysis result by the image analyzing section 14, and extracts case data having a similar image.

Search of similar images is implemented by comparing the feature value of the image data on an area of interest inputted from the image analyzing section 14 with feature values of image data on the identical region registered into the database 18 to calculate a similarity degree between the image data and, determining images to be similar based on the calculated similarity degree.

As a method for calculating the similarity degree, there may be used a method involving use of methods for calculating the similarity degree of publicly known multi valued data, such as a difference of feature values, a least square distance on feature quantity space and a Mahalanobis' distance. When a discriminant function of a certain feature is used as a feature value, processing to narrow down similar image data that are identical discrimination results and to set priority thereon may be performed. Further, processing to narrow down similar image data identical in region and position information and to set priority thereon may also be performed.

The text data input section 20 is adapted to enable a user to input text data required for case data search, and is embodied by input devices, such as a keyboard and a mouse. Examples of the text data to be inputted include keywords, such as a disease name, image findings, a region, and patient information, though the text data is not limited thereto.

The text search section 16b compares text data inputted from the text data input section 20 with text information on respective case data stored in the database 18, and extracts case data including the text data that matches the inputted data. It is also possible to use a method for extracting not only the case data that completely matches the inputted text data, but also the case data that includes a term identical to the text data but in spells, such as a term "cancer" written in hiragana (Japanese syllabary character) that is identical, except in spells, to a term "cancer" written in kanji (Chinese character), and a term identical in meaning to the text data, such as "malignant tumor" that also means "cancer".

It is also possible to use general publicly known search methods, such as a method for extracting not only the data that completely matches a plurality of keywords but also the data that matches any one of the keywords.

The case search section 16 calculates final search results based on the search results by the image search section 16a and the search results by the text search section 16b. The final search results are the case data extracted in the text search section 16b and arranged in order of similarity degrees obtained in the image search section 16a.

Based on the search results by the case search section 16 (equivalent to the search result display device), pieces of information such as similar case images, related text information, and similarity degrees are displayed on the display section 22 (equivalent to the display device). A confirmation button for making a user select whether to refer to a search history or the like may also be displayed on the display section 22.

The search condition storage section 24 (equivalent to the search condition storing device) stores, as a search history of image searches, extraction results of areas of interest by the area extraction section 12, as well as image analysis results (feature values of areas of interest) by the image analyzing section 14 and text data inputted from the text data input section 20 as a search history of text searches if necessary. The search condition storage section 24 may also be configured to store not only a search history but also a search result history at the same time.

<Operation of Case Search Device>

A description is now given of operation of the case search device 1 configured as shown above. First, operation of a general case search is explained with reference to the flow chart of FIG. 3.

First, a user inputs image data, which is a diagnosis target, from the image data input section 10 (Step S1 equivalent to the image acquisition step). The user also inputs text data on the diagnosis target image from the text data input section 20 (Step S2 equivalent to the text data acquisition step).

The text search section 16b searches for case data registered into the database 18 based on the text data inputted from the text data input section 20 (Step S3), and extracts all the case data that include related text data (Step S4 equivalent to the search step).

The area extraction section 12 executes automatic extraction of an area of interest from the image data inputted from the image data input section 10 (Step S5 equivalent to the area extraction step), while the image analyzing section 14 calculates a feature value of the area of interest extracted by the area extraction section 12 (Step S6).

Next, the image search section 16a performs an image search against a plurality of the case data extracted in Step S4 based on the feature value calculated in Step S6 (Step S7 equivalent to the search step). In this step, a similarity degree between the image data based on the feature value is calculated, and ranking of the calculated similarity degrees (order of similarity degrees) is determined.

The case search section 16 displays search results on the display section 22 (Step S8 equivalent to search result display step). In this step, the case data extracted in the text search section 16b are displayed in order of the similarity degrees obtained in the image search section 16a.

At the same time, the case search section 16 (equivalent to the search history display device) indicates on the display section 22 each of the search condition of the image search section 16a and the search condition of the text search section 16b, i.e., a coordinate representing the area of interest that was automatically extracted by the area extraction section 12 and the text data inputted into the text data input section 20 (Step S9 equivalent to the search history display step).

Finally, the search condition storage section 24 stores each of the above-stated search condition of the image search section 16a and search condition of the text search section 16b (Step S10 equivalent to the search condition storage step). It is also possible to store not only the search conditions but also the search results.

Figure 4:
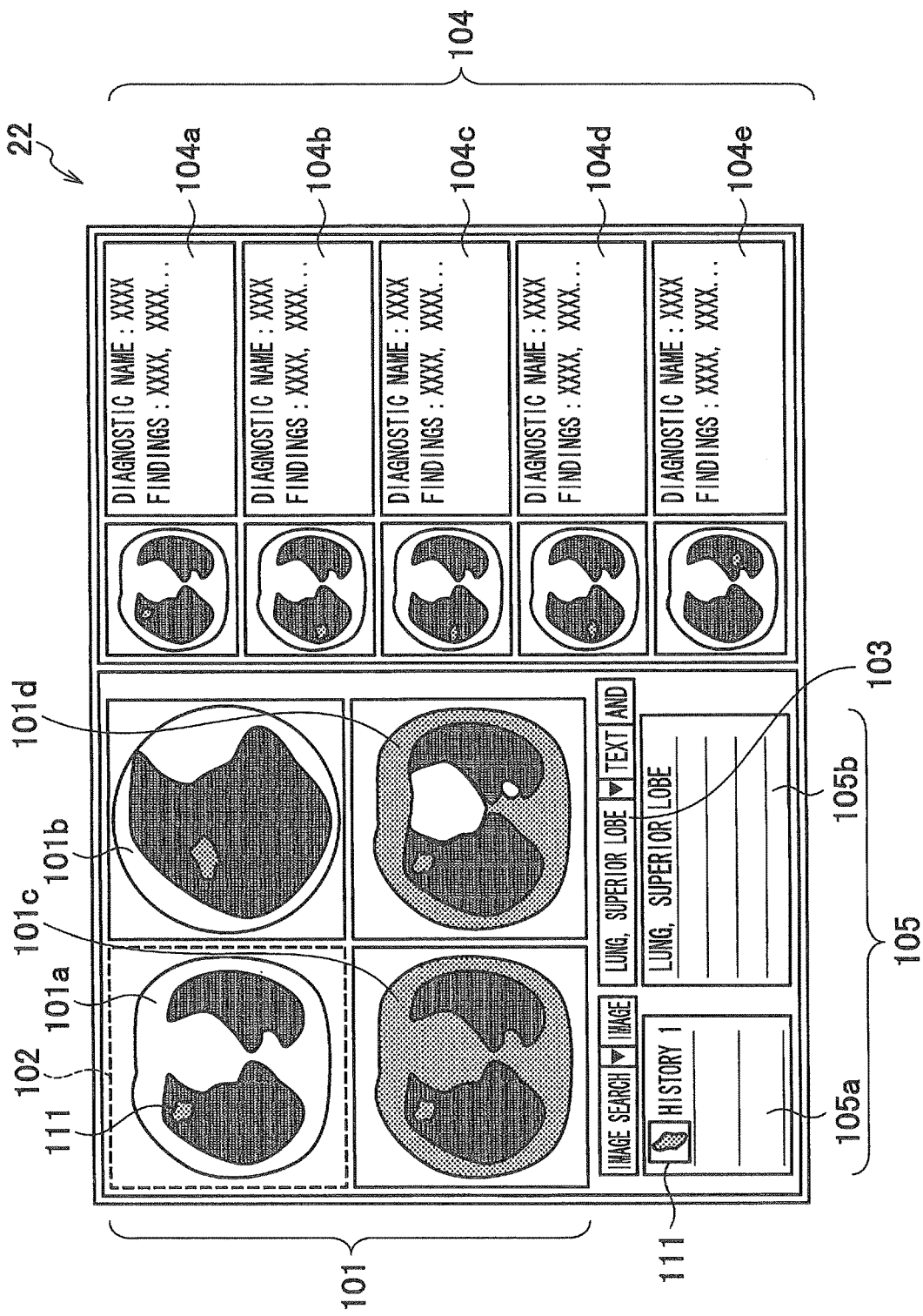
FIG. 4 is a view showing one example of search result and search history indication.

FIG. 4 is a view showing one example of a screen displayed on the display section 22 in this case.

Reference numeral 101 on the upper left part of FIG. 4 designates an examination data display area, where four diagnosing images including diagnosing images 101a, 101b, 101c and 101d are displayed therein.

Among these, the diagnosing image 101a encircled with a broken line 102 serves as a target image subjected to extraction of an area of interest by the area extraction section 12. The broken line 102 can be moved by using an arrow key on a keyboard, a mouse or the like, so that the user can select a desired diagnosing image.

In the present embodiment, four diagnosing images 101a to 101d or the diagnosing image 101a encircled with the broken line 102 may be considered as the image inputted into the image data input section 10.

A specified area 111 inside the diagnosing image 101a is an area of interest of the diagnosing image 101a automatically extracted by the area extraction section 12. As described before, the area of interest 111 may manually be extracted.

Reference numeral 103 on the lower middle part of FIG. 4 designates a text box placed in a search condition input area, which corresponds to the text data input section 20 in FIG. 1. The user can perform a text search for the case data registered into the database 108 by inputting text data into the text box 103 with use of a keyboard or the like.

Reference numeral 104 on the right part of FIG. 4 designates a search result display area. In the drawing, case data each including a diagnosing image and text data or diagnostic information is displayed for five case data including case data 104a, 104b, 104c, 104d, and 104e as search results. The degrees of similarity of these five case data to the area of interest 111 are higher in the order of the case data 104a, 104b, 104c, 104d and 104e.

Reference numeral 105 on the lower left part of FIG. 4 designates a search history display area, which includes an image search history area 105a and a text search history area 105b. In this drawing, the first search has been completed, so that the shape of the area of interest 111 that is a search condition for an image search is displayed in the image search history area 105a and the text data of "lung, superior lobe" that is a text search condition is displayed in the text search history area 105b.

Processing to search for the same inputted image 101a as explained with reference to FIG. 3 may be repeated with varied search conditions. For example, by inputting new text data from the text data input section 20, a new search may be performed. A new search may also be implemented by performing extraction with the shape of the area of interest being changed.

Figure 3:
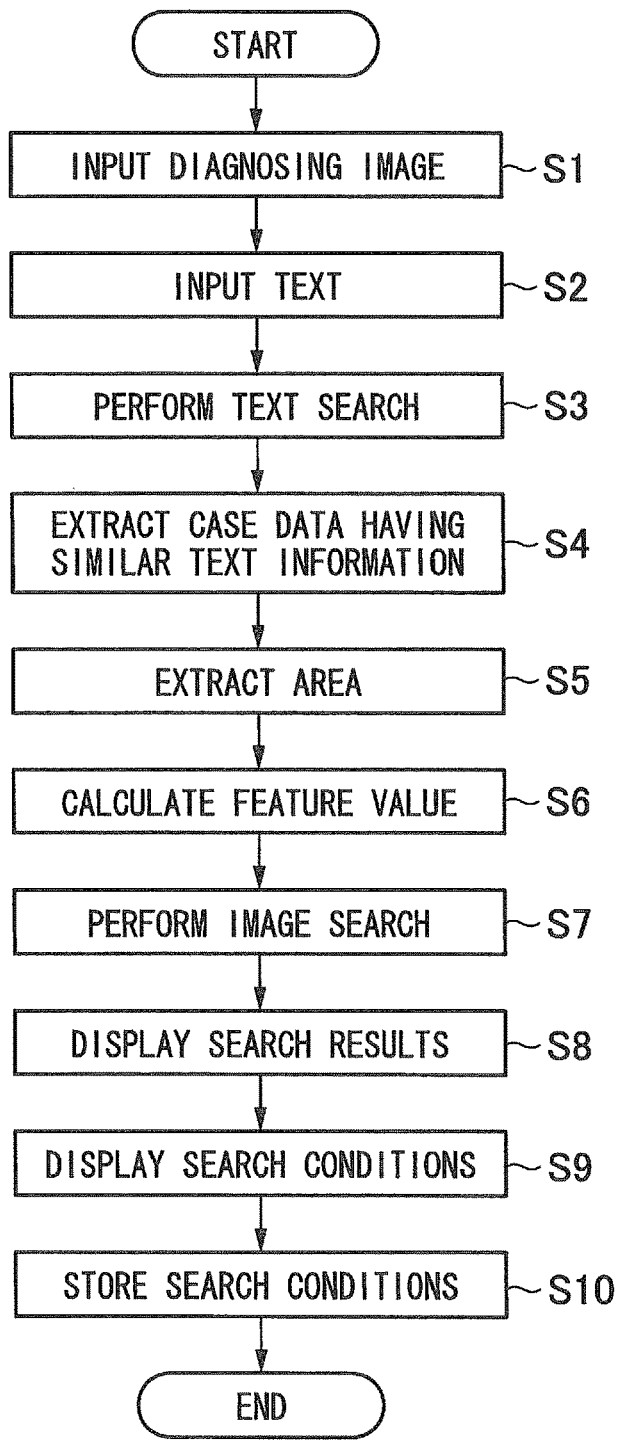
FIG. 3 is a flow chart showing case search processing.
Figure 5:
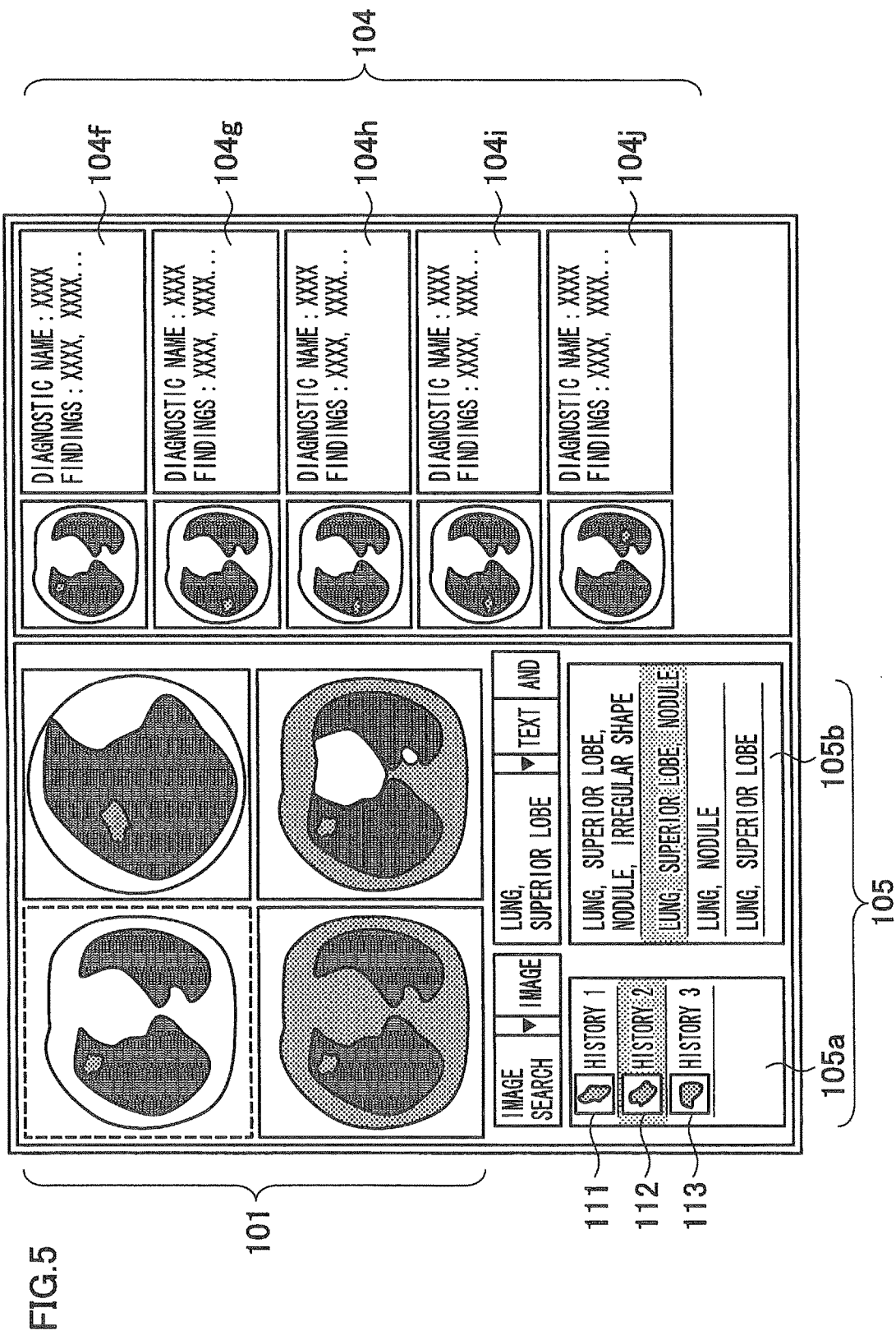
FIG. 5 is a view showing one example of search result and search history indication.

FIG. 5 is a view showing one example of a screen displayed on the display section 22 at the time of repeating the processing shown in FIG. 3. In this drawing, as a history of image search conditions, three conditions including an area of interest 111, an area of interest 112, and an area of interest 113 are displayed in the image search history area 105a. As a history of text conditions, four conditions including "lung, superior lobe, nodule, irregular shape", "lung, superior lobe, nodule", "lung, nodule", and "lung, superior lobe" are displayed in the text search history area 105b.

<Case Search Processing Using Search History>

Figure 6:
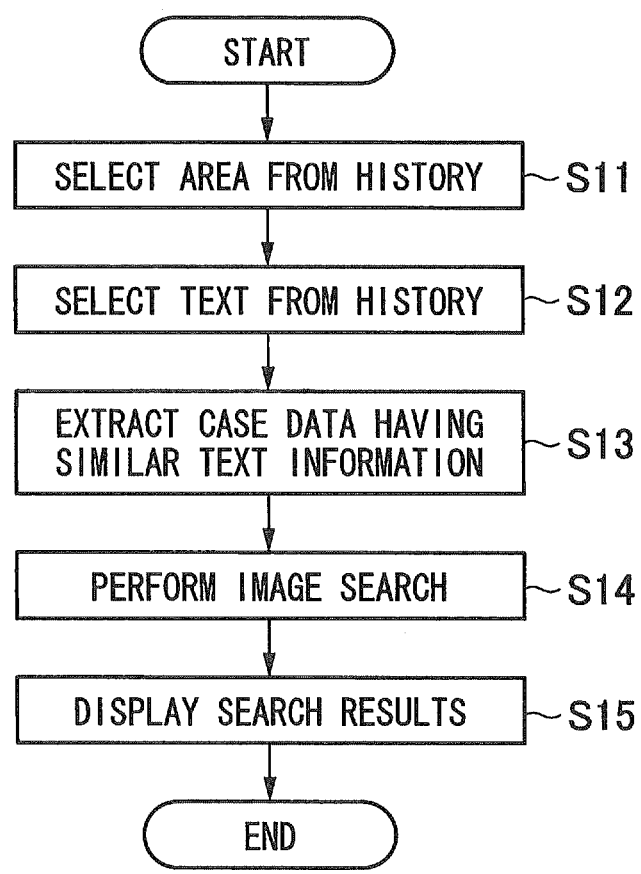
FIG. 6 is a flow chart showing case search processing with use of a search history.

A description is now given of the operation of a case search with use of a search condition displayed in the search history display area 105 with reference to the flow chart of FIG. 6.

First, a user selects a desired search condition from a history of image search conditions currently displayed in the image search history area 105a (Step S11).

In an example shown in FIG. 5, the area of interest 112 is selected out of the area of interest 111, the area of interest 112, and the area of interest 113 which are displayed in the image search history area 105a.

Next, a desired search condition is selected from a history of text search conditions currently displayed in the text search history area 105b (Step S12).

In the example shown in FIG. 5, "lung, superior lobe, nodule" is selected out of conditions including "lung, superior lobe, nodule, irregular shape", "lung, superior lobe, nodule", "lung, nodule", and "lung, superior lobe" which are displayed in the text search history area 105b.

Once a text search condition and an image search condition are selected, the text search section 16b in the case search section 16 searches for case data registered in the database 18 based on the selected text search condition "lung, superior lobe, nodule", and extracts all the case data that include related text data (Step S13).

The image search section 16a further performs an image search against a plurality of the case data extracted in Step S13 based on the feature value of the area 112 previously calculated (Step S14).

When a combination of the selected text search condition and the image search condition is a combination used in a past search, and a history of the search results is stored in the search condition storage section 24, the past search results may be read from the search condition storage section 24 instead of re-execution of a search in the case search section 16.

Finally, the case search section 16 displays search results on the search result display area 104 (Step S15). In the example shown in FIG. 5, case data each including a diagnosing image and text data or diagnostic information is displayed for five case data including case data 104*f,* 104*g,* 104*h,* 104*i,* and 104*j* as search results. In this example, the degrees of similarity to the area of interest 112 are higher in order of the case data 104*f,* 104*g,* 104*h,* 104*i,* and 104*j.*

Thus, it becomes possible to perform a case search with use of a search condition that was used before. According to the present embodiment, a history of search conditions for an image search and a history of search conditions for a text search are each separately stored and displayed, so that a search can be performed based on the conditions freely combined. A program for causing a computer to execute a case search is also included in the present invention.

Although the search histories of both the image search conditions and the text search conditions are used in this embodiment, it is also possible to select one of the conditions out of the search histories and to newly input the other condition to implement a search.

<Other Display Forms>

Figure 7:
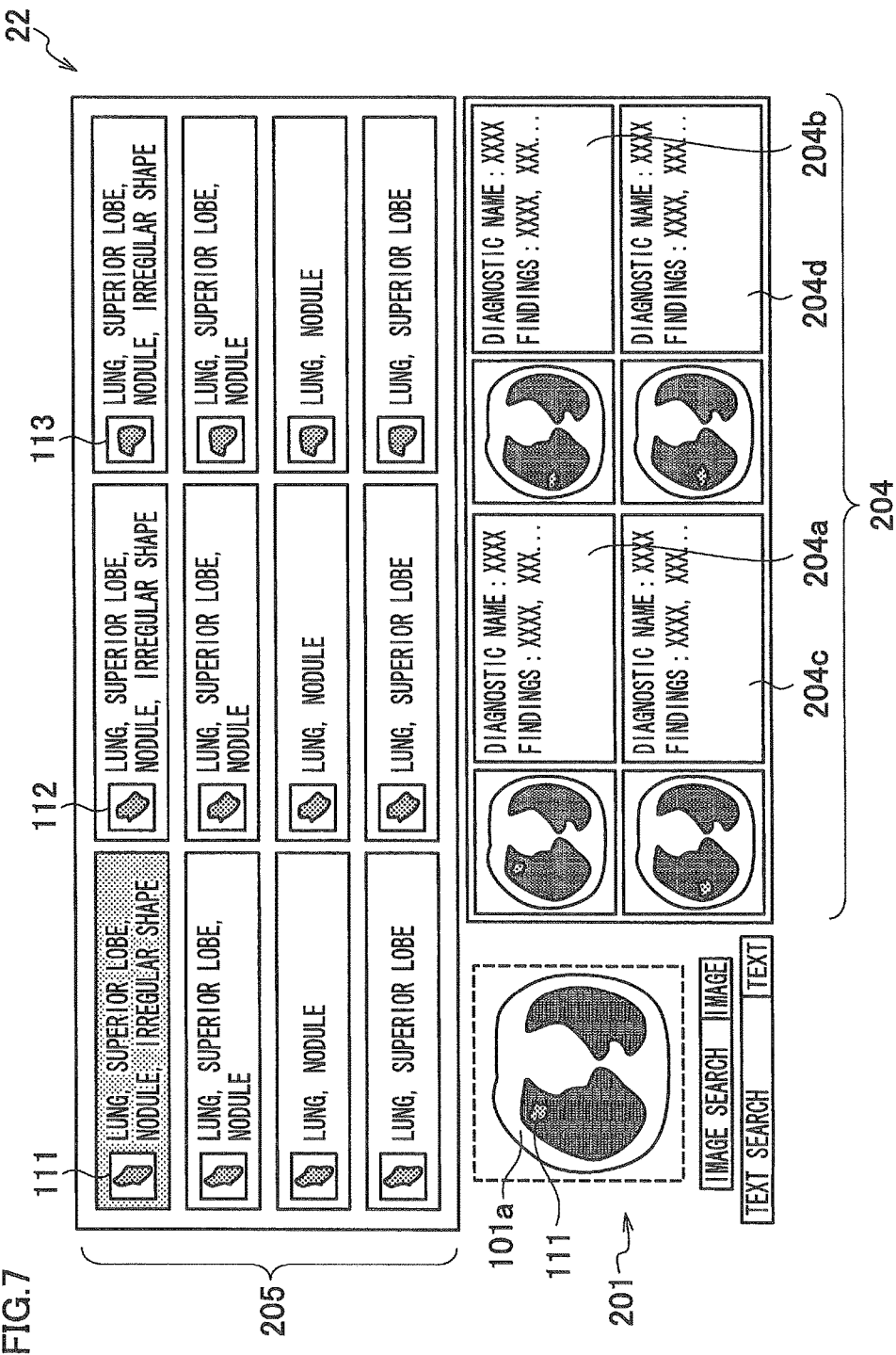
FIG. 7 is a view showing one example of search result and search history indication.

FIG. 7 is a view showing another embodiment of search result and search history indication.

Reference numeral 201 on the lower left part of FIG. 7 designates an examination data display area, where a diagnosing image 101*a* is displayed in this case.

Reference numeral 204 on the lower part of FIG. 7 designates a search result display area. In the drawing, case data each including a diagnosing image and text data or diagnostic information is displayed for four case data including case data 204*a* to 204*d* as search results.

Reference numeral 205 on the upper part of FIG. 7 designates a search history display area. In the search history display area 205, search conditions in the image search history and search conditions in the text search history are displayed in a matrix form. For example, in the image search history displayed in a matrix, the search conditions in a left column correspond to the area of interest 111, the search conditions in a central column correspond to the area of interest 112, and the search conditions in a right column correspond to the area of interest 113.

In the text search history, the search conditions in an uppermost line correspond to "lung, superior lobe, nodule, irregular shape", the search conditions in the second line correspond to "lung, superior lobe, nodule", the search conditions in the third line correspond to "lung, nodule" and the search conditions in a lowermost line correspond to "lung, superior lobe". Therefore, for example, a cell of the central column in the third line represents a search under the image search condition being an area 112 and the text search condition being "lung, nodule".

When the user specifies the cell of the central column in the third line with a mouse or the like, a search under the image search condition being an area 112 and the text search condition being "lung, nodule" is executed, and a result thereof is displayed in the search result display area 204.

If all the search conditions in the search history are used in indication in a matrix form, the screen may be crammed with information. Therefore, only a specified number of latest search conditions may be displayed in a matrix form.

Figure 8:
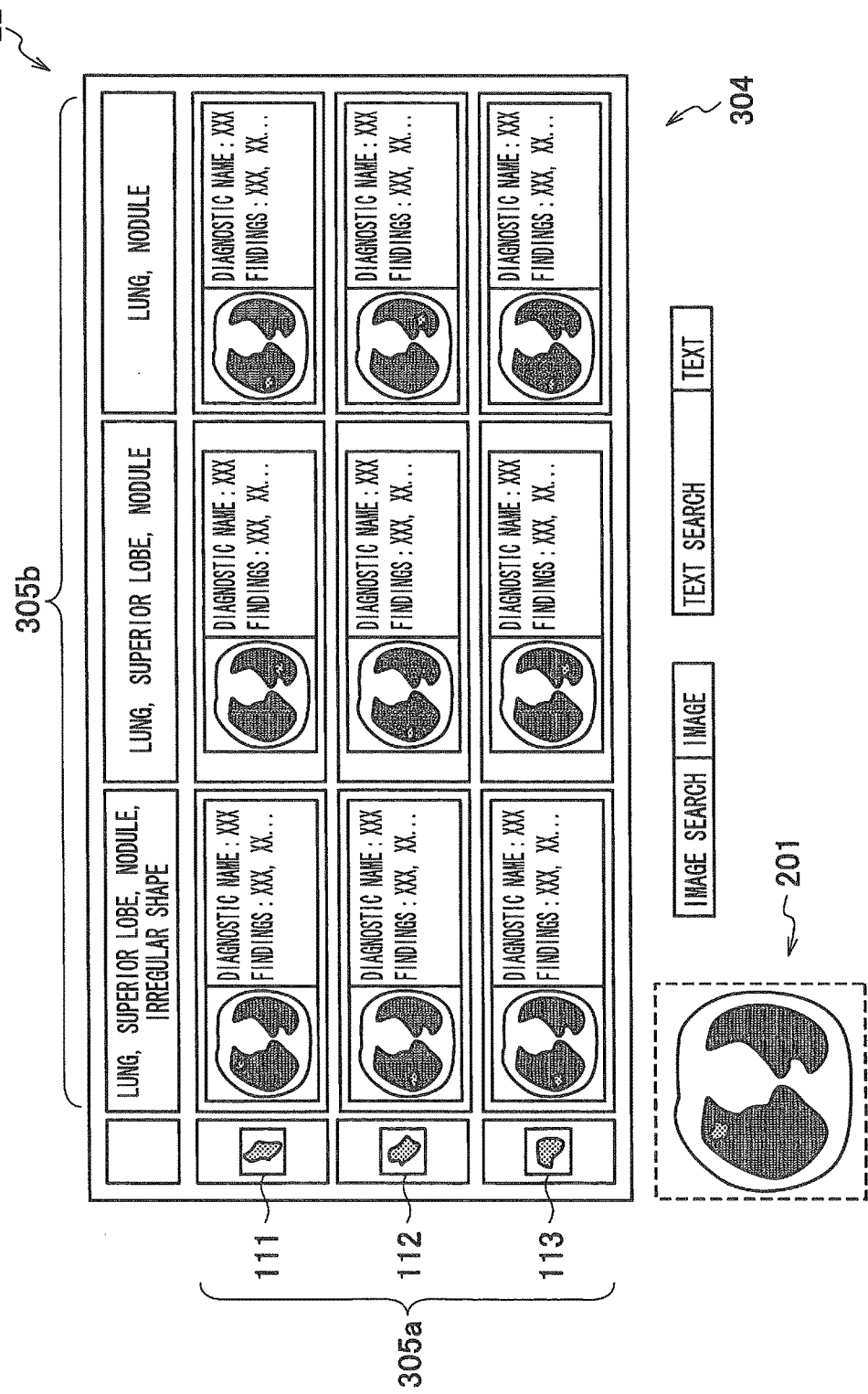
FIG. 8 is a view showing one example of search result and search history indication.

FIG. 8 is a view showing an example of the search results displayed in a matrix form.

A left column in the matrix portion of FIG. 8 serves as an image search history area 305*a,* while an upper line portion serves as a text search history area 305*b.* A search result in each combination is displayed, one result per combination, in a search result display area 304 in the matrix. In this area, out of the case data extracted in the text search section 16*b,* case data having a highest similarity degree obtained in the image search section 16*a* is each displayed.

It is to be noted that the display form is not limited to one configuration but may freely be changed by the user.

What is claimed is:

1. A case search device, comprising:
a database which stores case data including image data and text data;
a display device;
a controller comprising a central processing unit, the central processing unit configured to execute:
an image acquiring unit configured to acquire a diagnosis target image;
an area extracting unit configured to extract different areas of interest with different extraction conditions of a same location in areas of interest from the acquired diagnosis target image;
a text data acquiring unit configured to acquire text data relating to the diagnosis target image;
a search device unit configured to perform against the database an image search with the extracted area of interest as an image search condition and a text search with the acquired text data as a text search condition and to extract case data that matches the image search condition and the text search condition;
a search result display unit configured to display the extracted case data on the display device;
a search condition storing unit configured to store image search conditions of respectively different areas of interests regarding a same diagnosis target image with which case data is extracted more than once by the search unit and the text search condition; and
a search history display unit configured to display each of the stored image search conditions and text search conditions as a combination with a single result per combination of the image search condition and the text search condition on the display device in a search result display matrix so as to be specifiable by a user,
wherein when any one of the displayed image search conditions and any one of the displayed text search conditions are specified, the search unit extracts case data that matches the specified image search condition and the specified text search condition,
wherein the search unit:
calculates a feature value regarding the extracted area of interest by:
calculating pixel values including:
an average value, a distribution, a maximum value, a minimum value and a luminance histogram within image data;
positions;
numeric values with respect to shapes including a circularity degree of a profile, a moment, a cross sectional radius, a volume, and an area; and
shape information and texture information on the lesion portion in the area of interest:
compares the calculated feature value with a feature value of image data on an identical region in the case data included in the database to calculate a similarity degree by using one of:
a difference of feature values;
a least square distance on feature quantity space; and
a Mahalanobis' distance; and performs an image search based on the calculated similarity degree, and wherein the search result display unit displays a coordinate representing the area of interest that was automatically extracted and the text data inputted into the text data input section.

2. The case search device according to claim 1, wherein the area extracting unit extracts the area of interest based on an instruction by the user.

3. The case search device according to claim 1, wherein the area extracting unit extracts the area of interest by conducting image analysis based on a specified threshold.

4. The case search device according to claim 1, wherein the text data acquiring unit acquires text data inputted by the user with an input device.

5. The case search device according to claim 1, wherein the search unit extracts case data from the case data obtained by the text search in order of higher similarity degrees.

6. The case search device according to claim 1, wherein the search condition storing unit stores the calculated feature value as the image search condition.

7. The case search device according to claim 1, wherein the search condition storing unit stores a search result by the search device.

8. The case search device according to claim 1, wherein the search history display unit displays the stored image search conditions and text search conditions in a matrix on the display device.

9. The case search device according to claim 1, wherein the search result display unit displays image data and text data in the extracted case data.

10. A method for case search including a controller comprising a central processing unit, the method comprising:

an image acquisition step of acquiring a diagnosis target image;

an area extraction step of extracting different areas of interest with different extraction conditions of a same location in areas of interest from the acquired diagnosis target image;

a text data acquisition step of acquiring text data relating to the diagnosis target image;

a search step of performing against a database storing case data including image data and text data an image search with the extracted area of interest as an image search condition and a text search with the acquired text data as a text search condition and extracting case data that matches the image search condition and the text search condition;

a search result display step of displaying the extracted case data on a display device;

a search condition storage step of storing image search conditions of respectively different areas of interest regarding a same diagnosis target image with which case data are extracted more than once by the search step and the text search condition in a storing device; and a search history display step of displaying on the display device each of the stored image search conditions and text search conditions as a combination with a single result per combination of the image search condition and the text search condition in a search result display matrix so as to be specifiable by a user, wherein, in the search step, when any one of the displayed image search conditions and any one of the displayed text search conditions are specified, case data that matches the specified image search condition and the specified text search condition is extracted, wherein the central processing unit executes the image acquisition step, the area extraction step, the text data acquisition step, the search step, the search result display step, the search condition storage step, and the search history display step, wherein the search step:

calculates a feature value regarding the extracted area of interest by:

calculating pixel values including:

an average value, a distribution, a maximum value, a minimum value and a luminance histogram within image data;

positions;

numeric values with respect to shapes including a circularity degree of a profile, a moment, a cross sectional radius, a volume, and an area; and shape information and texture information on the lesion portion in the area of interest;

compares the calculated feature value with a feature value of image data on an identical region in the case data included in the database to calculate a similarity degree by using one of:

a difference of feature values:

a least square distance on feature quantity space; and a Mahalanobis' distance; and performs an image search based on the calculated similarity degree, and wherein the search result display step displays a coordinate representing the area of interest that was automatically extracted and the text data inputted into the text data input section.

11. A non-transitory programmable storage medium tangibly embodying a program of machine-readable instructions executable by a digital processing apparatus to perform a case search method, said method comprising:

an image acquiring function to acquire a diagnosis target image;

an area extracting function to extract different areas of interest with different extraction conditions of a same location in areas of interest from the acquired diagnosis target image;

a text data acquiring function to acquire text data relating to the diagnosis target image;

a search function to perform against a database storing case data including image data and text data an image search with the extracted area of interest as an image search condition and a text search with the acquired text data as a text search condition and to extract case data that matches the image search condition and the text search condition;

a search result display function to display the extracted case data on a display device;

a search condition storing function to store image search conditions of respectively different areas of interest regarding a same diagnosis target image with which case data are extracted more than once by the search function and the text search condition in a storing device; and a search history display function to display on the display device each of the stored image search conditions and text search conditions as a combination with a single result per combination of the image search condition and the text search condition in a search result display matrix so as to be specifiable by a user, wherein in the search function, when any one of the displayed image search conditions and any one of the displayed text search conditions are specified, case data that matches the specified image search condition and the specified text search condition is extracted,
wherein the search function:
  calculates a feature value regarding the extracted area of interest by:
    calculating pixel values including:
      an average value, a distribution, a maximum value, a minimum value and a luminance histogram within image data;
      positions;
      numeric values with respect to shapes including a circularity degree of a profile, a moment a cross sectional radius, a volume, and area; and
      shape information and texture information on the lesion portion in the area of interest;
  compares the calculated feature value with a feature value of image data on an identical region in the case data included in the database to calculate a similarity degree by using one of:
    a difference of feature values;
    a least square distance on feature quantity space; and
    a Mahalanobis' distance; and
  performs an image search based on the calculated similarity degree, and
wherein the search result display function displays a coordinate representing the area of interest that was automatically extracted and the text data inputted into the text data input section.

12. The case search device according to claim 1, further comprising an image analyzing device configured to analyze image data on the area of interest extracted by the area extraction device, and configured to calculate a feature value required for the image search.

13. The case search device according to claim 12, wherein, a search of similar images is implemented by comparing the feature value of the image data on the area of interest inputted from the image analyzing device with feature values of image data on an identical region registered into the database to calculate a similarity degree between the image data and, determining images to be similar based on the calculated similarity degree.

14. The case search device according to claim 1, wherein, when a combination of the text search condition and the image search condition is a combination used in a past search, and a history of the search results is stored in the search condition storage unit, the past search results are read from the search condition storage unit.

15. The case search device according to claim 1, wherein, when a combination of the text search condition and the image search condition is a combination used in a past search, and a history of the search results is stored in the search condition storage unit, the past search results are read from the search condition storage unit without a re-execution of a search in the case search unit.

* * * * *